United States Patent [19]
Nelson et al.

[11] Patent Number: 5,246,859
[45] Date of Patent: Sep. 21, 1993

[54] METHOD OF STABILIZING A CARBON DIOXIDE SENSOR

[75] Inventors: Alan Nelson, San Diego; Henry K. Hui, Laguna Niguel; Monte Bennett, Escondido; Soonkap Hahn, San Diego; Charles S. Bankert, Oceanside; Jeffrey T. Jackson, Poway, all of Calif.

[73] Assignee: Puritan-Bennett Corporation, Carlsbad, Calif.

[21] Appl. No.: 888,550

[22] Filed: May 22, 1992

Related U.S. Application Data

[63] Continuation-in-part of Ser. No. 597,816, Oct. 15, 1990, abandoned.

[51] Int. Cl.$^5$ .......................... G01N 31/00; G01N 1/18
[52] U.S. Cl. ............................... 436/11; 436/18; 436/127; 436/133; 436/178; 73/1 R; 73/23.21; 204/403
[58] Field of Search ............. 436/11, 18, 8, 127, 436/133, 178; 73/1 R, 23.21; 204/403

[56] References Cited

U.S. PATENT DOCUMENTS

| | | | |
|---|---|---|---|
| 3,754,867 | 8/1973 | Guenther | 23/254 R |
| 3,824,157 | 7/1974 | Macur | 204/1 T |
| 3,884,640 | 5/1975 | Lock et al. | 23/253 R |
| 4,469,792 | 9/1984 | Simmonds et al. | 436/11 |
| 4,485,174 | 11/1984 | Chiang et al. | 436/11 |
| 4,567,748 | 2/1986 | Klass et al. | 73/1 G |
| 4,689,308 | 8/1987 | Gerhard | 436/18 |
| 4,722,904 | 2/1988 | Feil | 436/11 |
| 5,045,529 | 9/1991 | Chiang | 514/6 |

OTHER PUBLICATIONS

Wolfbeis and Weis, *Fiber-Optic Fluorosensor for Oxygen and Carbon Dioxide*, pp. 2028-2030, vol. 60, 1988.
Munkholm and Walt, *A Fiber-Optic Sensor for $CO_2$ Measurement*, pp. 109-112, vol. 35, 1988.
U.S. Dept of Health and Human Services, *Fiber-Optic Carbon Dioxide Partial Pressure Sensor*, pp. 1-12, Mar. 1, 1983.

*Primary Examiner*—James C. Housel
*Assistant Examiner*—N. Bhat
*Attorney, Agent, or Firm*—Fulwider Patton Lee & Utecht

[57] ABSTRACT

The method of stabilizing a carbon dioxide sensor involves formulation of a bicarbonate buffer solution in the sensor with a bicarbonate ion concentration of from about 100 mM to about 200 mM bicarbonate. The method also involves treatment of the sensor to reduce the instability that may occur in carbon dioxide sensors when such sensors are exposed to either very low or very high carbon dioxide levels for extended periods of time. The sensor is treated by exposing the sensor to an aqueous solution containing at least 2 weight percent carbon dioxide, for from several days to several months. The solution may be prepared in advance, or may be dynamically infused with carbon dioxide to provide the desired carbon dioxide content.

21 Claims, No Drawings

METHOD OF STABILIZING A CARBON DIOXIDE SENSOR

RELATED APPLICATIONS

This application is a continuation in part of copending Ser. No. 07/597,816, filed Oct. 15, 1990, now abandoned in favor of File-Wrapper continuation Ser. No. 07/933,884 filed Aug. 21, 1992, now U.S. Pat. No. 5,204,265.

BACKGROUND OF THE INVENTION

1. Field of the Invention

This invention is generally directed to chemical and biochemical analysis of an analyte in a fluid or gaseous mixture, and more specifically relates to an intravascular carbon dioxide sensor stabilized against non-specific drift in measurements of carbon dioxide, and methods of stabilizing measurements taken with such an intravascular carbon dioxide sensor.

2. Description of Related Art

Measurement of acidity (pH) and the tension or partial pressure of carbon dioxide and oxygen in the blood have become important in modern medicine, particularly with regard to determining the respiratory condition of a patient. Although electrodes have been developed which are capable of making such measurements, they are generally of limited use in the medical field. Optical sensors for taking intravascular measurements of acidity, carbon dioxide and oxygen levels in the blood have also been developed, based upon the principle of enclosing a fluorescent indicator within a membrane permeable to the analyte to be measured, coupled to one or more optical fibers for measuring the intensity of fluorescence from the indicator. Since the fluorescence reaction of appropriately chosen indicators is altered according to the level of acidity, carbon dioxide, or oxygen being measured, these sensors allow remote measurement of these parameters when combined with compatible intravascular catheter systems.

A fiber optic chemical sensor may also be used for measuring pH by the use of optical absorbance indicators, such as phenol red, which may be chemically bound in the sensor. In this type of pH sensor, green and red light typically emerge from one optical fiber into the sensor, passing through the dye, to be reflected back through an optical fiber to a detector system. The green light is absorbed by the base form of the indicator, and the red light is not absorbed by the indicator, so that the red light may be used as an optical reference. The ratio of green to red light can then be measured, and related to pH.

A fluorescent indicator may be used in a similar fashion, with light in one wavelength region being used to excite the fluorescent indicator dye to emit light of a different wavelength. Such optical pH sensors typically include a fluorescent indicator dye, such as fluorescein or hydroxypyrenetrisulfonic acid (HPTS), placed over the tip of an optical fiber and a membrane cover over the dye which is permeable to the hydronium ions to be measured. The dye fluoresces when exposed to a certain wavelength of light conducted to it by the optical fiber. In practice, a pH sensor is fabricated by immobilizing a pH sensitive dye into a matrix attached to the distal end of the fiber. The dye is typically capable of existing in two forms, an anionic or base form, and a protonated or acid form. The two forms are each excited by a different frequency, but fluoresce at the same frequency, with the output responsive to excitation at the appropriate different frequencies being proportional to the pH of the sample to which the sensor is exposed. In this manner, measurement of the intensity of fluorescence of the indicator dye can be related to pH. A clinically useful range for measuring carbon dioxide as a blood gas parameter has been found to be from about 1.4 weight percent to about 15 weight percent carbon dioxide. Therefore, it is desirable for a carbon dioxide sensor to be accurate and repeatable over at least this range.

It has been found that carbon dioxide sensors frequently become destabilized when exposed to low carbon dioxide levels, and that a progressive loss of fluorescent intensity occurs in sensors utilizing fluorescent indicators after exposure to high carbon dioxide concentrations. The instability of such fiber optic based carbon dioxide sensors when the sensors are exposed to either very low or very high carbon dioxide levels for prolonged periods of time, such as several days, frequently results in non-specific drift of measurements of carbon dioxide levels. For uses of a carbon dioxide blood gas sensor as an intravascular sensor, it is important that the carbon dioxide sensor be stable and display minimal drift in measurements of carbon dioxide concentrations for at least a 72 hour period of use as an intravascular sensor. Various factors such as the process of manufacture, incorporation into a multiparameter sensor device, sterilization and storage can result in destabilization of the carbon dioxide sensor chemistry producing undesirable problems of non-specific drift. In addition, such sensors can be destabilized by the entry of trace amounts of contaminants in calibration gases or other gases to which the sensor may be exposed. Furthermore, sensors can be destabilized if the internal pH of the sensor deviates substantially from the desired range of from about 7.0 to 8.0. It would therefore be desirable to provide a carbon dioxide blood gas sensor which mitigates this non-specific drift instability.

Conventional carbon dioxide blood gas sensors typically have contained a bicarbonate buffer solution with concentrations of bicarbonate ranging from about 1 mM to about 10 mM bicarbonate. Bicarbonate buffer concentrations exceeding 20 to 30 mM bicarbonate have been generally judged as not being useful due to apparent loss of sensitivity. However, it has now been found that substantially higher bicarbonate buffer concentrations can stabilize carbon dioxide blood gas sensors against non-specific drift in measurements of carbon dioxide. It would therefore be desirable to provide a carbon dioxide blood gas sensor that incorporates a buffer with such a higher concentration of bicarbonate that is both stable and sensitive in measurement of carbon dioxide concentrations. The present invention fulfills these needs.

SUMMARY OF THE INVENTION

Briefly, and in general terms, the present invention provides a new and improved carbon dioxide sensor which is stabilized against non-specific drift of measurements of concentrations of carbon dioxide in a fluid. The carbon dioxide sensor incorporates a bicarbonate buffer solution having a bicarbonate concentration of from about 30 mM to about 200 mM bicarbonate ions, and preferably has a buffer solution with a 100 mM bicarbonate ion concentration. The carbon dioxide sensor can be further stabilized against non-specific drift prior to use by exposing the sensor to a preparatory solution which is infused with elevated levels of carbon dioxide.

The present invention is thus directed to an improved carbon dioxide blood gas sensor with enhanced stability against non-specific drift in measurements of carbon dioxide by incorporation of a concentration of bicarbonate ions that was hitherto thought to interfere with sensitivity of the sensor. The invention also concerns a method of reducing the instability that may occur in carbon dioxide sensors when such sensors are exposed to either very low or very high carbon dioxide levels for extended periods of time. In the method of the invention, the sensor is exposed to high carbon dioxide levels for a period of time sufficient to allow the sensor to achieve measurement stability. The method of the present invention acts to decrease the initial time required to achieve drift stability compared to the use of a sensor which has not used the invention. The sensor is preferably retained in storage containers containing a solution which has been infused with a gas stream containing from 2 to 100 weight percent carbon dioxide for a period of time varying from several days to several weeks. One currently preferred method is to retain the sensor in a storage container in a prepared solution infused with approximately 8 weight percent carbon dioxide, thus statically maintaining the sensor at a carbon dioxide tension in the midrange of the physiologically significant range. It has been found that storage of the sensor in a solution which has been infused with from 2 to 100 weight percent carbon dioxide eliminates sources of non-specific long term drift that lead to inaccuracy in transduced carbon dioxide content measurements in applications in which the sensor is required to monitor arterial carbon dioxide for prolonged periods of time. This conditioning procedure also facilities faster calibration at the point of use by maintaining the sensor at a physiologically significant carbon dioxide tension immediately prior to use.

These and other objects and advantages of the invention will become apparent from the following detailed description, which illustrates, by way of example, the features of the invention.

DETAILED DESCRIPTION OF THE PREFERRED EMBODIMENTS

Problems of non-specific drift of carbon dioxide blood gas sensors have been observed in both in vitro and in vivo testing for sensor instability. According to a presently preferred embodiment of the method of the present invention, a carbon dioxide sensor is brought into a state of readiness by passive storage in a solution with a carbon dioxide tension in a physiologically significant range. In an alternative preferred embodiment, the sensor may be conditioned by a combination of exposure of the sensor to high carbon dioxide levels in a solution dynamically infused with a gas stream having very high to absolute carbon dioxide tension, followed by passive storage in another solution with a carbon dioxide tension in a physiologically significant range.

The present invention is particularly applicable for stabilizing measurements of the concentration of carbon dioxide in a fluid, such as blood, by a carbon dioxide sensor sensitive to changes in pH of a bicarbonate buffer immobilized in the sensor. A typical sensor incorporates a dye material such as fluorescein in a polymeric matrix, such as silicone, which is permeable to carbon dioxide in the blood. The sensor is typically placed at the end of an optical fiber, which may be inserted into the vasculature of a patient for in vivo blood gas measurements. The sensor is of the type sensitive to changes in pH, and the matrix material is generally soaked in a bicarbonate solution to incorporate the solution in the matrix material, or the sensor otherwise incorporates the bicarbonate solution, which serves as a buffer according to the well known equation:

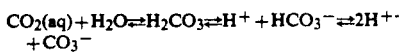

The bicarbonate buffer solution is preferably formulated to contain a concentration of from about 30 mM to about 200 mM bicarbonate ions, and is most preferably formulated to contain a concentration of about 100 mM bicarbonate ions. The bicarbonate buffer may, for example, be an aqueous solution formulated with a bicarbonate salt such as sodium bicarbonate, potassium bicarbonate, cesium bicarbonate, and the like, a carbonate salt such as sodium carbonate, potassium carbonate, cesium carbonate, and the like, or combinations thereof. Experiments have shown that carbon dioxide blood gas sensors containing such high concentrations of bicarbonate ions dramatically increase the stability of the sensor and minimize drift of measurements of carbon dioxide concentrations without significantly lowering the sensitivity or response time of the sensor.

According to one further preferred method of preparation of the carbon dioxide sensor of the invention for use, the carbon dioxide sensor can be stored in a sealed container having an aqueous solution which preferably has a relatively high partial pressure of carbon dioxide. The aqueous solution also is preferably osmotically adjusted to approximately match the osmotic pressure or osmolarity of the fluid, typically blood, in which the sensor will eventually be used. The solution is preferably prepared in advance, although it is also possible to infuse the solution with the proper carbon dioxide content after the sensor is placed in the solution.

The aqueous solution preferably should have at least a 2 weight percent carbon dioxide content, and can be prepared by infusing the solution with a gas stream containing from 2 to 100 weight percent carbon dioxide, with the balance being inert gas, such as nitrogen, to infuse the second solution with a physiologically significant carbon dioxide tension. The aqueous solution in which the sensor is to be stored is preferably infused with a gas containing approximately 8 weight percent carbon dioxide, with the balance of the gas being inert gas. The storage solution is also preferably osmotically adjusted to be approximately equivalent to the osmotic strength of the fluid in which the carbon dioxide sensor will eventually be used. The sensor is typically stored in a sealed container with the storage solution for at least one day, and preferably from several days to several months, to condition the sensor for calibration and use.

In another preferred embodiment, a carbon dioxide sensor according to the invention may optionally be preliminarily exposed to a preparatory aqueous solution prior to storage in a second aqueous solution. In this two step process, the sensor is exposed to a preparatory aqueous solution, while a gas stream having a relatively high partial pressure of carbon dioxide, and preferably approximately 100 weight percent carbon dioxide, is periodically or continuously dynamically infused into the solution by bubbling the gas stream in the solution for an hour to a few days as desired.

The sensor is then stored in the second aqueous solution having a 2 weight percent carbon dioxide content of approximately 2 weight percent or more. The second solution in which the sensor is to be stored is preferably prepared in advance, but may optionally be dynamically prepared after the sensor has been placed in the solution by infusing a gas stream containing from 2 to 100 weight percent carbon dioxide, with the balance being inert gas, such as nitrogen, to infuse the second solution with a physiologically significant carbon dioxide tension. The physiologically significant range of carbon dioxide concentration for the gas stream is typically from 2 weight percent to 15 weight percent carbon dioxide, with the balance of the gas being inert gas, and the secondary aqueous solution is preferably infused with a gas containing approximately 8 weight percent carbon dioxide, with the balance of the gas being inert gas. The secondary solution is also preferably osmotically adjusted to be approximately equivalent to the osmotic strength of the fluid in which the carbon dioxide sensor will eventually be used. The sensor is then typically stored in a sealed container with the second solution to which the sensor is exposed for at least one day, and preferably from several days to several months, to condition the sensor for calibration and use.

It has been found that carbon dioxide sensors such as those discussed above provide substantially stabilized measurements of carbon dioxide tension for in vitro and in vivo blood gas measurements, not exhibiting the previously observed non-specific drift in measurements of either low or high carbon dioxide levels in solutions for prolonged periods of time in excess of 72 hours. The method also enables faster calibration at the point of use by maintaining the sensor at a physiologically significant carbon dioxide tension.

It should be recognized that other forms of carbon dioxide sensors, such as pH electrodes measuring changes in pH of bicarbonate buffers, or similar buffers, may also be stabilized in the manner of the invention.

It will be apparent from the foregoing that, while particular forms of the invention have been described, various modifications can be made without departing from the spirit and scope of the invention. Accordingly, it is not intended that the invention be limited, except as by the appended claims.

What is claimed is:

1. A method of stabilizing a carbon dioxide blood gas sensor for measuring a physiologically significant range of concentrations of carbon dioxide in a fluid, the sensor having a matrix permeable to carbon dioxide gas, the matrix including a dye indicator material sensitive to changes in pH, the sensor having a measurable response which is sensitive to changes in the dye indicator material due to changes in concentration of carbon dioxide gas, comprising:
   incorporating an aqueous bicarbonate buffer solution in said matrix, said bicarbonate buffer solution having a concentration of at least about 100 mM bicarbonate ion.

2. The method of claim 1, wherein said bicarbonate buffer solution has a bicarbonate ion concentration of from about 100 mM to about 200 mM.

3. The method of claim 1, further including the step of exposing the sensor to a concentration of between 2 weight percent and 100 weight percent of carbon dioxide for at least one day.

4. The method of claim 3, wherein said step of exposing said sensor to a concentration of carbon dioxide comprises:
   storing said sensor in a sealed container for a period of at least one day with an aqueous treatment solution containing a gas consisting of from 2 weight percent to 100 weight percent of carbon dioxide with the balance of the gas being inert.

5. The method of claim 3, wherein said step of exposing said sensor to a concentration of carbon dioxide comprises storing said sensor in a sealed container for a period of at least one day in an aqueous treatment solution into which a gas is bubbled, the gas consisting essentially of from 2 weight percent to 100 weight percent carbon dioxide with the balance being inert gas.

6. The method of claim 5, wherein said treatment solution is saturated with a gas consisting essentially of 100 weight percent carbon dioxide.

7. The method of claim 4, wherein said treatment solution is saturated with a gas consisting essentially of 100 weight percent carbon dioxide.

8. The method of claim 4, wherein said solution is adjusted to have substantially the same osmotic pressure as blood.

9. The method of claim 4, wherein prior to said step of storing said sensor in said aqueous treatment solution, said sensor is exposed to a preparatory aqueous solution containing a concentration of at least 2 weight percent carbon dioxide for at least one hour.

10. The method of claim 4, wherein prior to said step of exposing said sensor to the aqueous treatment solution, said sensor is exposed to an aqueous preparatory solution into which a gas stream is bubbled for at least one hour, the gas stream consisting essentially of 100 weight percent carbon dioxide.

11. The method of claim 1, where said step of incorporating said aqueous bicarbonate buffer solution in said matrix comprises soaking said matrix in said aqueous bicarbonate buffer solution.

12. A method of stabilizing measurement of the concentration of carbon dioxide in a fluid by a sensor which is sensitive to changes in pH in the sensor, said sensor including at least one dye indicator which when exposed to an energy of excitation exhibits a fluorescence which is altered by carbon dioxide to provide a measurable fluorescence response, comprising:
   incorporating an aqueous bicarbonate buffer solution in the sensor, the buffer solution having a bicarbonate ion concentration of from about 100 mM to 200 mM; and
   exposing the sensor to an aqueous treatment solution infused with a gas consisting essentially of from 2 weight percent to 100 weight percent carbon dioxide, with the balance of the gas being inert gas, for at least one day.

13. The method of claim 12, wherein prior to said step of exposing said sensor in said aqueous treatment solution, said sensor is exposed to a preparatory aqueous solution containing a concentration of at least 2 weight percent carbon dioxide for at least one hour.

14. The method of claim 12, wherein prior to said step of exposing said sensor to the aqueous solution, said sensor is exposed to an aqueous solution dynamically infused with a gas stream consisting essentially of 100 weight percent carbon dioxide for at least one hour.

15. The method of claim 12, wherein said aqueous solution is infused with essentially 100 weight percent carbon dioxide.

16. A method of stabilizing an optical fiber carbon dioxide sensor adapted for measurement of the concentration of carbon dioxide in a fluid, the sensor including a matrix permeable to carbon dioxide gas, the matrix including a dye indicator material sensitive to changes in pH, comprising the steps of:

incorporating an aqueous bicarbonate buffer solution in the sensor, the buffer solution having a bicarbonate ion concentration of from about 100 mM to 200 mM;

exposing the sensor to a first aqueous solution infused with a relatively high concentration of carbon dioxide for at least one hour; and exposing the sensor for at least one day to a second aqueous solution infused with a fluid consisting essentially of from 2 weight percent to 100 weight percent of carbon dioxide, with the balance of the fluid being inert.

17. The method of claim 16, wherein the sensor is exposed to the first aqueous solution while the first aqueous solution is dynamically infused by bubbling the first aqueous solution with a gas stream consisting essentially of 100 weight percent of carbon dioxide.

18. The method of claim 16, wherein the first solution is adjusted to have substantially the same osmotic pressure as blood.

19. The method of claim 16, wherein the second aqueous solution is infused with a gas consisting essentially of from 2 weight percent to 15 weight percent of carbon dioxide, with the balance of the gas being inert.

20. The method of claim 16, wherein the second aqueous solution is infused with a gas consisting essentially of approximately 8 weight percent carbon dioxide, with the balance of the gas being inert.

21. The method of claim 16, wherein the aqueous bicarbonate buffer solution contains a source of bicarbonate ions selected from the group consisting of sodium bicarbonate, potassium bicarbonate, cesium bicarbonate, sodium carbonate, potassium carbonate, cesium carbonate, and combinations thereof.

* * * * *